United States Patent
Agerup et al.

(10) Patent No.: US 7,942,930 B2
(45) Date of Patent: May 17, 2011

(54) BIOCOMPATIBLE IMPLANT SYSTEM AND METHOD

(75) Inventors: Bengt Agerup, Paris (FR); Ninus Caram-Letham, Uppsala (CH); Ulf Winter, Uppsala (CH)

(73) Assignee: Q-Med AB, Uppsala (SE)

( * ) Notice: Subject to any disclaimer, the term of this patent is extended or adjusted under 35 U.S.C. 154(b) by 448 days.

(21) Appl. No.: 11/812,205

(22) Filed: Jun. 15, 2007

(65) Prior Publication Data
US 2008/0312739 A1 Dec. 18, 2008

(51) Int. Cl.
*A61F 2/12* (2006.01)
*A61F 2/44* (2006.01)

(52) U.S. Cl. .......................... 623/8; 623/17.12
(58) Field of Classification Search ........... 623/8, 17.12; 606/191–192
See application file for complete search history.

(56) References Cited

U.S. PATENT DOCUMENTS

| | | | | |
|---|---|---|---|---|
| 4,904,260 A * | 2/1990 | Ray et al. | | 623/17.12 |
| 4,936,858 A * | 6/1990 | O'Keeffe | | 623/8 |
| 4,963,150 A * | 10/1990 | Brauman | | 623/8 |
| 5,011,494 A * | 4/1991 | von Recum et al. | | 623/23.74 |
| 5,116,371 A * | 5/1992 | Christensen et al. | | 623/23.67 |
| 5,219,360 A * | 6/1993 | Georgiade | | 623/8 |
| 5,344,451 A * | 9/1994 | Dayton | | 623/8 |
| 5,425,762 A * | 6/1995 | Muller | | 623/11.11 |
| 5,632,774 A | 5/1997 | Babian | | |
| 5,676,698 A * | 10/1997 | Janzen et al. | | 623/8 |
| 5,713,960 A * | 2/1998 | Christensen et al. | | 523/113 |
| 6,022,376 A * | 2/2000 | Assell et al. | | 623/17.16 |
| 6,913,626 B2 * | 7/2005 | McGhan | | 623/23.73 |
| 2002/0193448 A1 * | 12/2002 | Wallace et al. | | 514/772.4 |
| 2005/0281880 A1 * | 12/2005 | Wang | | 424/486 |

FOREIGN PATENT DOCUMENTS

| | | |
|---|---|---|
| WO | WO-2005/097218 A | 10/2005 |
| WO | WO-2006/133569 A | 12/2006 |
| WO | WO 2006133569 A1 * | 12/2006 |

* cited by examiner

*Primary Examiner* — Corrine M McDermott
*Assistant Examiner* — Andrew Iwamaye
(74) *Attorney, Agent, or Firm* — Birch, Stewart, Kolasch & Birch, LLP.

(57) ABSTRACT

The invention relates to an implantable combination comprising a barrier (12), and a macromolecular bio-compatible material (14). The barrier (12) is porous to allow moieties of the macromolecular bio-compatible material (14), when implanted, to be exposed through the barrier, whereby the surface of the barrier is experienced by the body as an essentially non-foreign object. It also relates to an implant made from a barrier material and a bio-compatible material, the implant being suitable as e.g. a breast implant.

18 Claims, 4 Drawing Sheets

US 7,942,930 B2

BIOCOMPATIBLE IMPLANT SYSTEM AND METHOD

Figure 1:
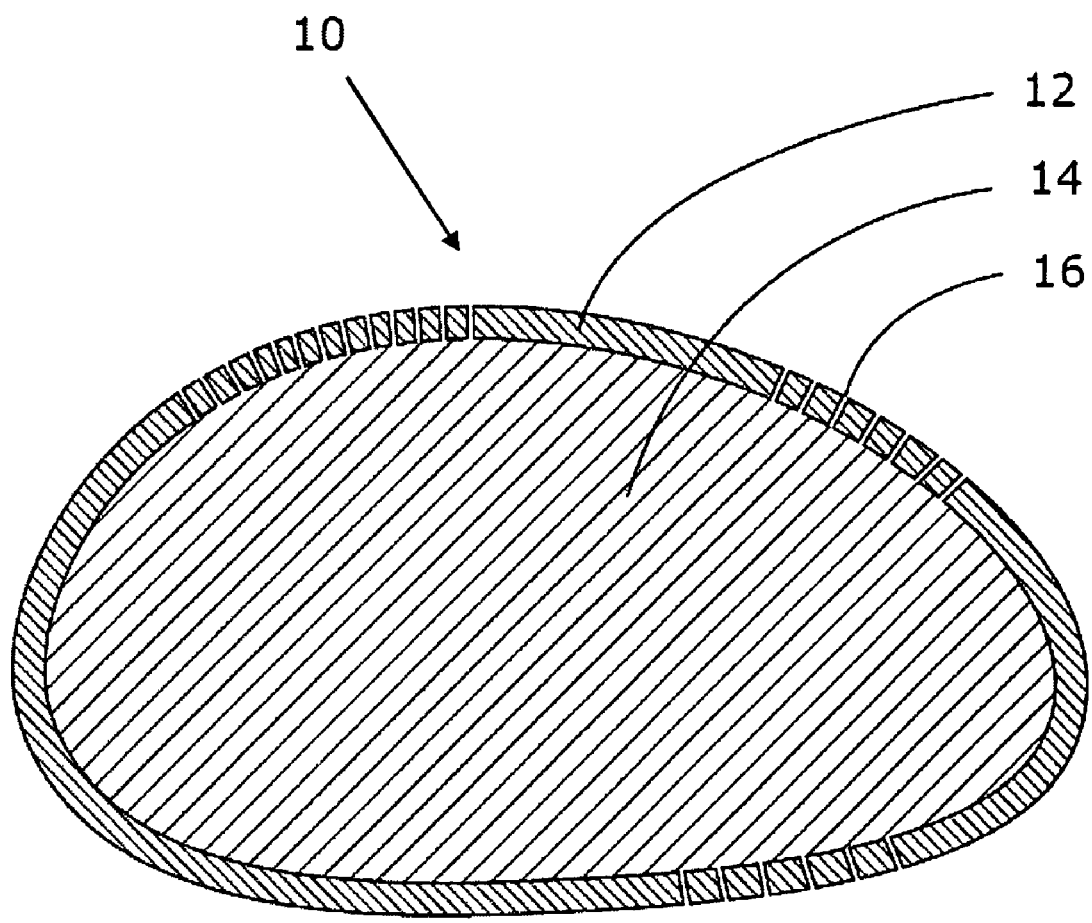

The present invention relates to biocompatible implants in a general sense, in particular to the provision of implants exhibiting a surface that prevents e.g. connective tissue to grow on and adhere to the implant.

BACKGROUND OF THE INVENTION

When a foreign object (such as an implant) is introduced into a living (e.g. human or animal) body, i.e. in contact with the tissue therein, the body will react thereto. Typically the body will react by trying to reject the object by expelling it. If this is not possible the object is instead encapsulated in connective tissue so as to "exclude" it from the body.

The actual reaction or response obtained will depend on where in the body the object is introduced. Also, the manner of introducing the foreign object and the degree of damage that is inflicted upon the subject (human or animal), caused by the procedure itself will have an impact.

Furthermore, the material that the object is made of and the residence time of the foreign object in the body will be of importance for the reaction that is developed.

Many types of implants have been developed in the medical science, e.g. substitutes for bone such as titanium joints. Titanium is known to be very biocompatible in that it does not cause rejection reactions. It also has the property of easily being incorporated in the surrounding skeletal tissue in a desirable manner.

However, for certain types of implants rather the opposite is desirable, namely that the implant should not be incorporated into the surrounding tissue, and should absolutely not allow connective tissue to adhere thereto. One example is breast (or mammary) implants.

There are several different types of prior art breast implant. A common type is a silicon pad formed to the desired shape and consistency, as exemplified by U.S. Pat. No. 5,632,774 (Babian). Another common type is based on saline, sometimes also including solid filler materials such as silicon beads, enclosed in a bag or pouch. An example is disclosed in U.S. Pat. No. 5,554,671 (Waybreight et al). There are numerous other types based on combinations of these and other types of implant.

In the prior art there are disclosures of various methods of modifying the surface of such bags or pouches in order to increase their bio-compatibility for reducing or eliminating the encapsulation effect mentioned above. Such surface modification can be to physically treat the surface to modify the surface structure or chemically by binding chemical entities to the surface to provide a more bio-compatible surface.

In EP 0 696 210 (le Pesteur et al) there is disclosed the use of hydrogels based on hyaluronic acid and/or polydeoxiribonucleotides as materials for filling prostheses.

In US application No. 2002/0193448 A1 (Wallace et al) there is disclosed use of fragmented polymeric compositions, in particular hydrogels of proteins, polysaccharides or non-biological polymers, for e.g. controlled release of drugs.

None of the prior art documents known to the inventors address the issue of protecting an implant inside the body from being rejected or encapsulated or coated by connective tissue by providing an implant exhibiting a protective layer of bio-compatible material exposed on and/or through the surface of the implant, that is sustained over time and/or continuously renewed over time, so as to prevent and/or inhibit on-growth by cells, such as connective tissue. In fact, it is a well established notion that implants should not be allowed to "bleed", i.e. leakage should not be allowed at all.

SUMMARY OF THE INVENTION

In view of the drawbacks of the prior art implants, the object of the present invention is to provide an implantable device comprising a barrier material for keeping a bio-compatible and preferably bioresorbable material, in particular a hydrogel, in place at a selected location in the body of a mammal, such as a human being, said barrier material exhibiting openings allowing moieties of the biocompatible material to be exposed through the barrier material to the effect that the body will experience the implanted structure as a non-foreign object. Thereby on-growth of cells, such as connective tissue, i.e. encapsulation thereof is inhibited or preferably prevented.

Thus, a first aspect of the invention, defined in claim 1, provides an implantable combination comprising a barrier and a macromolecular bio-compatible material the barrier is porous to allow moieties of the macromolecular bio-compatible material, when implanted, to be exposed through the barrier, whereby the surface of the barrier is experienced by the body as an essentially non-foreign object.

A second aspect the invention, defined in claim 16, is an implant comprising a macromolecular bio-compatible material, enclosed in a pouch made of a barrier material which is porous to allow moieties of the hydrogel, when implanted, to be exposed through the barrier, whereby the surface of the barrier is experienced by the body as an essentially non-foreign object.

A third aspect of the invention, defined in claim 19, is a depot device, for sustained or controlled release of a drug or other beneficial agent, comprising a barrier; a macromolecular and bio-compatible material; a drug distributed in the macromolecular and bio-compatible material. The barrier material is porous to allow moieties of the macromolecular and bio-compatible material, when implanted, to be exposed through the barrier, whereby the surface of the barrier is experienced by the body as an essentially non-foreign object, and to allow the drug to be released through the barrier.

In a further aspect there is provided a kit, defined in claim 20, comprising a barrier and a macromolecular and bio-compatible material, wherein the barrier material is porous to allow moieties of the hydrogel, when implanted, to be exposed through the barrier.

There is also provided a method of body contouring, defined in claim 21, by implanting a suitably shaped implant, comprising positioning an implantable combination as claimed in claim 1 in a desired location in a body, suitably by minimal invasive surgery.

Figure 2:
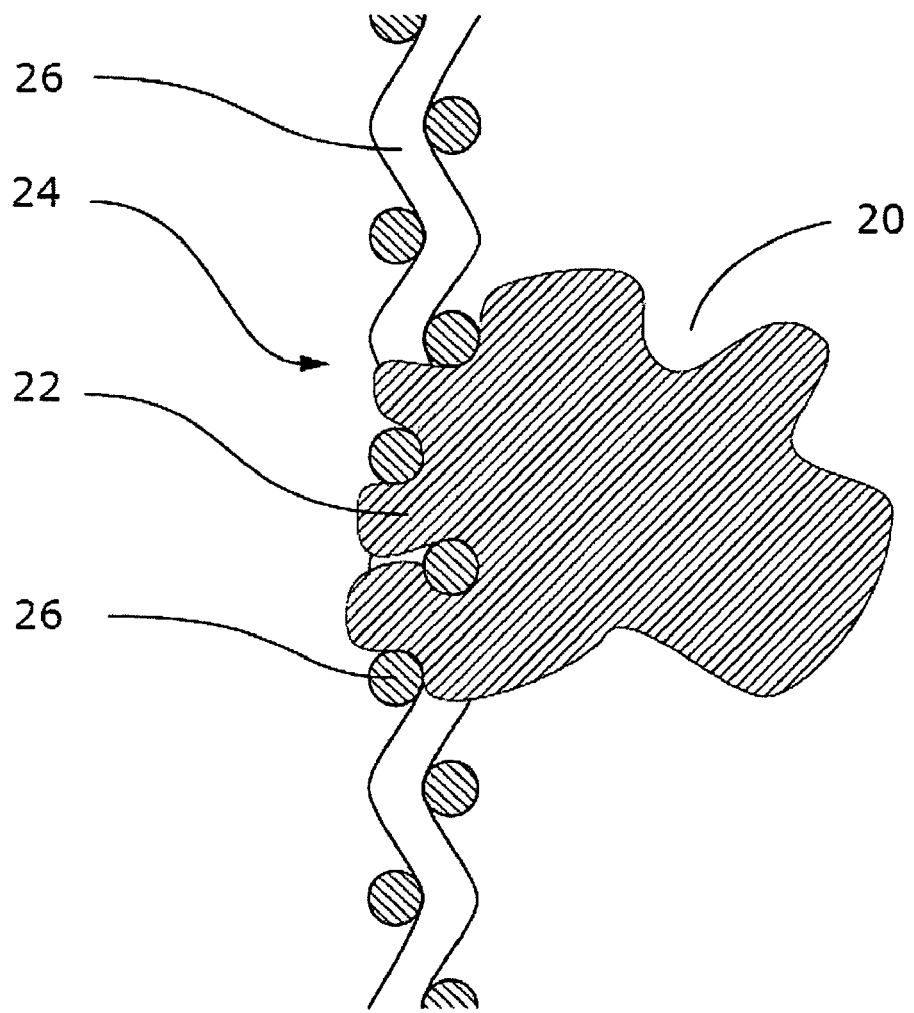
Figure 3:
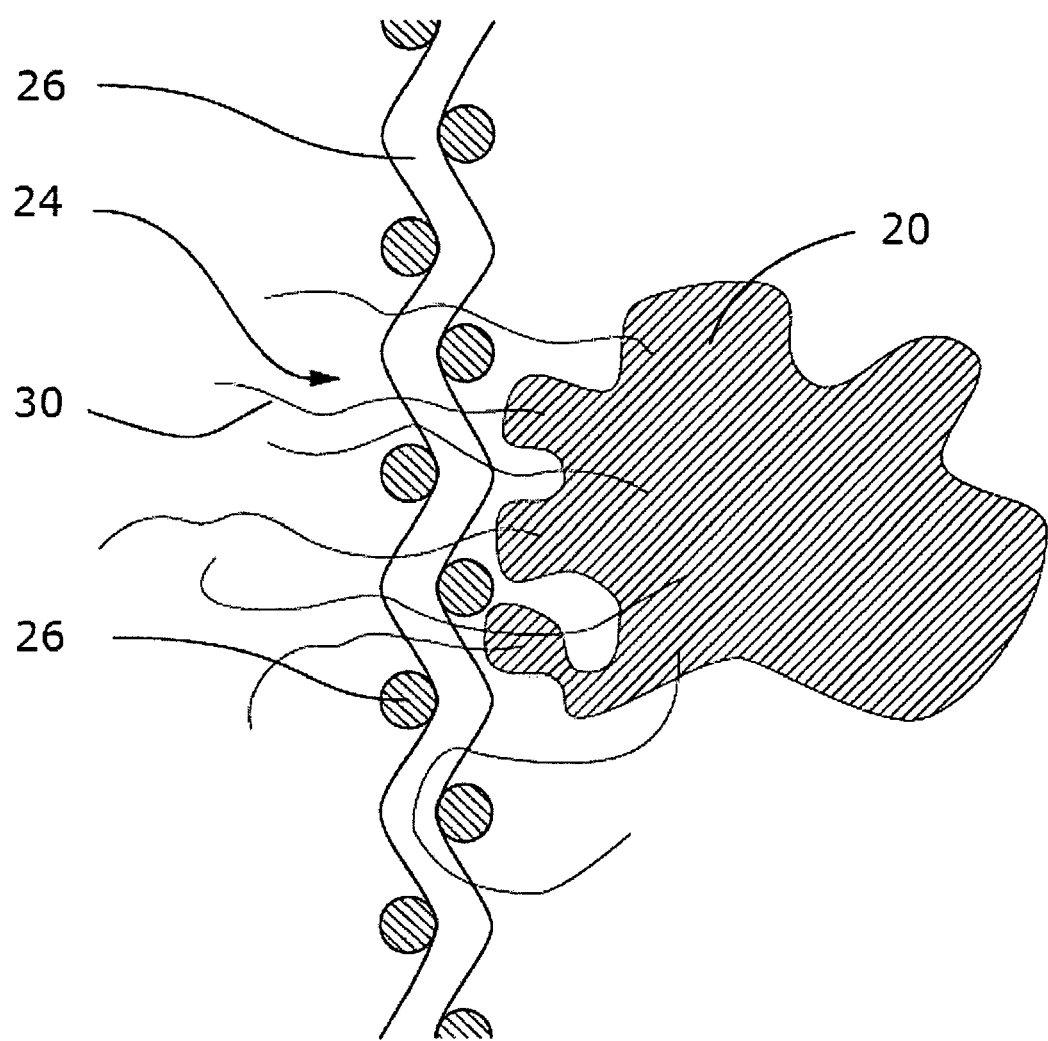
Figure 4:
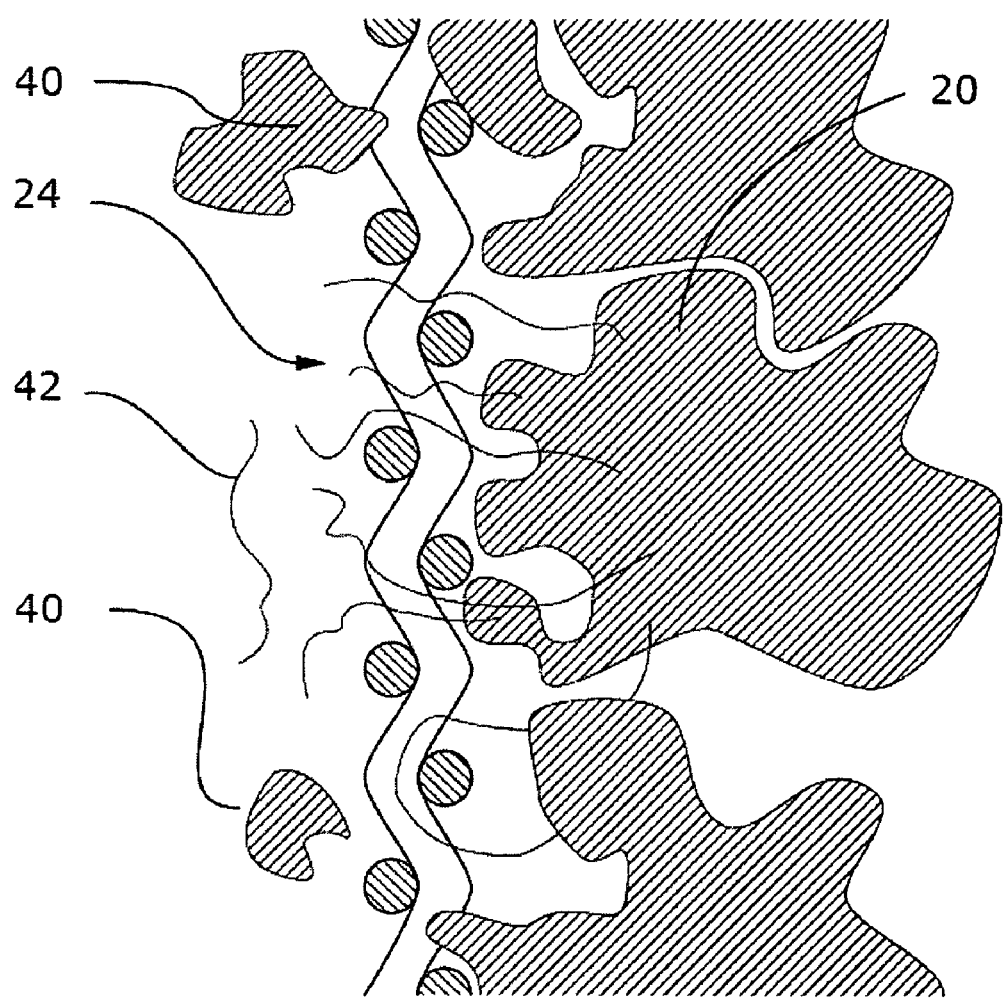

Further scope of applicability of the present invention will become apparent from the detailed description given hereinafter and the accompanying drawings which are given by way of illustration only, and thus not to be considered limiting on the present invention, and wherein FIG. 1 schematically illustrates a breast implant according to the present invention; and FIG. 2 is a schematic illustration of a plausible mechanism for achieving a bio-compatible surface on an implant, where a viscoelastic particle extends through a mesh in a woven barrier and is exposed through it;

FIG. 3 is a schematic illustration of a further mechanism that causes a bio-compatible surface on an implant; and FIG. 4 is a schematic illustration of a still further mechanism for achieving a bio-compatible surface on an implant.

DETAILED DESCRIPTION OF PREFERRED EMBODIMENTS

The present invention is based on the idea of providing an implantable structure or device, comprising a bio-compatible and bio-degradable/resorbable material usable as an implant, hereinbelow referred to as "implant material", in combination with a porous barrier material. The implant material will be exposed through the barrier material to provide a bio-compatible surface when implanted, so that the response from the body will be at least reduced, preferably significantly reduced.

This idea is implemented by using a barrier material (examples of which are commercially available), exhibiting a "porosity", to contain a bio-compatible material, in preferred embodiments suitably a viscoelastic and particulate hydrogel, in order to keep it in a desired location. By "porosity" and "porous" for the purposes of this application we mean that the material exhibits more or less well defined holes or passages through which solvent (e.g. water) and small molecules and/or particles can pass without hindrance, but which excludes larger particles from passing through.

Without wishing to be bound by theory, it is believed that the porosity enables moieties of the bio-compatible material, be it a viscoelastic and particulate hydrogel or even only a macro-molecular material, by deformation due to its viscoelasticity or simply by leaking or bleeding through the material, to extend (slightly) out through the pores. A proviso is of course e.g. in the case of hydrogel particles, that they must be large enough not to deform to an extent that they can "slip through" the pores. For a "simple" macromolecule the pores must be substantially smaller in order that the "bleeding" out of the material be slow enough to maintain the shape of an implant over extended periods of time.

In this way, i.e. the presence of the bio-compatible material on or at or at least exposed through the barrier, the barrier material will not be experienced by the body tissue as a foreign object, but instead the body will identify the surface as a bio-compatible surface, and thus encapsulation by connective tissue will be prevented or at least be retarded or reduced.

Again, without wishing to be bound by theory, it is believed that another mechanism could also be responsible for the bio-compatibility of the structure according to the invention. Namely, that degradation products from the bio-compatible implant material will migrate or diffuse through the pores, and form a protective layer on or adjacent the surface of the barrier material enclosing or shielding off the implant material.

Thus, what happens is that moieties of the bio-compatible material, e.g. hydrogel, will be "seen" by the body through the barrier, because the pores in the barrier will expose the hydrogel. By "moiety" we mean a small portion of the material, e.g. a hydrogel particle, either in the form of a "dendrite" or other extension thereof, or molecular chains extending from the bio-compatible material, such as the hydrogel particles, and out through the pores, but still bonded to the particle. It is important to remember that the hydrogel particles may have very irregular shapes, and can comprise elongated portions of a size that might easily extend into and out from the pores in the barrier material. By "moiety" we also mean small fragments or decomposition products of the material, e.g. the hydrogel, of a size easily allowing such fragments to pass through the pores.

Both of the above discussed possible mechanisms are referred to as "bleeding" in this application. "Bleeding" can therefore generally be defined as the process/processes occurring when a bio-compatible material, such as a particulate hydrogel in a swollen state, or a macromolecular material in general, is enclosed in a porous container or pouch, by any of the mechanisms discussed above.

For the purpose of this application a "pore" is taken to mean openings in a sheet material, such as a fabric, be it woven, knitted, non-woven or in the form of a perforated (or discontinuous, i.e. having openings extending through) film. Thus, a pore can be the mesh openings in a woven or knitted material as well as interstices in a non-woven fibre cloth. The requirement that is placed on these pores is that they must enable the processes and conditions described above.

Of course it is most likely that a combination of these two phenomena will bring about the bio-compatibility.

The rate of degradation of the implant material is suitably controlled by cross-linking the constituent polymer molecules in a controlled manner to a desired degree. Also the size of the particles will play a roll in the rate of material transportation through the barrier materials.

Thus, a barrier material having the mentioned properties allows particles and/or fragments or molecules of bio-compatible and resorbable implant materials to permeate through the barrier to an extent and rate that there is formed a steady state and continuously renewed layer of coating on the barrier material outer surface that will limit the natural response of the body to reject the implanted entity. In other words, the barrier material is not in direct contact with the tissue in the body, thereby reducing or even eliminating the response against the foreign object.

In another implementation it is conceivable to use the inventive concept in a situation where some tissue, e.g. an organ or a gland or the like, has been removed. Suppose it is desirable to maintain the body cavity formed upon removal of said organ. It would then be possible to attach a barrier material over the cavity, e.g. by suturing or the like, and use it as local barrier for preventing or limiting the dissipation of the implant material. With the barrier in place one can inject a suitable hydrogel to fill up the void. When subsequently at a later point in time a replacement for the removed tissue is to be inserted, the hydrogel is simply removed and the body cavity will easily accommodate the new piece of tissue.

The implant material can also be used as a depot for controlled release of smaller molecules, such as drugs, entrapped inside the implant material. The release will occur slowly in conjunction with degradation of the implant material and the migration of degradation products will entrain the smaller molecules.

The barrier material is suitably a thin and flexible material with a porosity tailored to the size of the particles and/or the fragments or degradation products of the implant material, such that the migration through the barrier is controlled. In particular the barrier can be a woven or knitted material, but other porous materials such as non-woven or other types of fibre cloths are also possible.

The barrier material can be worked so as to form a container completely enclosing implant material. In this way the barrier material can be used to impart a structure to the enclosed implant material defined by the physical properties of the barrier material and its geometric shape.

Examples of conventional techniques that can be used for shaping the barrier material are thermoforming, injection moulding, rotational moulding, injection blow moulding, injection stretch blow moulding, extrusion blow moulding, insert moulding, vacuum forming.

In order to join materials or pieces of materials to form a suitable structure, any of the following techniques can be used: laser welding, ultrasonic welding, linear vibrating welding, orbital vibration welding, spin welding, hot plate welding. Other possible methods are sewing, stitching, gluing, stapling.

The introduction of the foreign object, i.e. the implant structure, can be achieved by a so called "minimal invasive medical procedure", which is defined as a procedure that is carried out by entering the body through the skin or through a body cavity or anatomical opening, but with the smallest damage possible to these structures.

It is also possible to design the container such that the final shape of the implanted object can be modified after having been introduced into the body. In particular the container can be refilled or replenished to adjust the volume to a desired size, e.g. if and when the implant material has degraded and thus been reduced in volume. Refilling can simply be done by injecting more material with a syringe, directly through the barrier material. Alternatively a dedicated valve or port in the barrier material can be used.

As already indicated, the barrier material can be of different types. The basic requirement is that it be permeable i.e. exhibit pores or interstices allowing small molecules or fragments of polymers to pass there through at controlled rates. Preferably, the barrier is a textile material, such as a woven, knitted or non-woven material, having a mesh size of more than 20 μm, preferably more than 30 μm. On the other hand the size should be less than 5 mm, preferably less than 1 mm, suitably less than 0.3 mm.

In the case of woven or knitted material suitably monofilament yarn is used. The monofilament yarn will have a yarn filament diameter in the range of larger than 20 μm, preferably 30 μm, but smaller than 4 mm, preferably smaller than 0.6 mm.

Examples of commercially available barrier materials usable in the invention are fabrics and filter mesh cloth from Sefar AG (polymer), SaatiTech S.P.A. (polymer), G. Bopp+ Co. AG (metal).

Although woven or knitted materials at present are preferred, it would be equally possible to utilize inherently non-porous materials that have been perforated by suitable means, so long as the properties of the barrier material meets the requirements of the invention.

The implant material suitable for use in the present invention can be selected from bio-compatible materials capable of forming particulate hydrogels.

Suitably the implant material is a viscoelastic and particulate hydrogel, preferably selected from biocompatible polysaccharides, and a particularly useful compound is cross-linked hyaluronic acid. The major volume of hydrogel particles should have a size, when subjected to a physiological salt solution, in the range of 0.1 to 10 mm, preferably 0.2 to 5 mm, more preferred 1 to 5 mm. An example of a prior art particulate hydrogel is disclosed in International Patent Publication WO 2005/097218 A2 (Ågerup).

The inventive concept can also be applied to make implantable depot devices for sustained and/or controlled release of a drug or any other beneficial agent, such as proteins and peptides. In such a case the implanted device can be fairly small, e.g like a flat tablet with a thickness of from about 1 mm to a few mm thick and having a "diameter" (in case of a circular tablet) of say 5-50 mm. these dimensions are only exemplary and other dimensions and shapes (e.g. square, rectangular, elliptic etc) are possible.

The implantable combination according to the invention can be supplied as a kit, comprising the barrier material and the bio-compatible material (e.g hydrogel) as separate kit components. The material, e.g. if it is a hydrogel, could be provided in dry form for restitution by the user, or ready for use in a sterile syringe. Such a kit is particularly suitable for the embodiment where the barrier is to be used as a membrane to confine hydrogel in a body cavity, as discussed above. The restitution need however not be performed by the user, but can take place inside the body after implanting.

Thus, the term "hydrogel" is taken to encompass both the dried state as well as the swollen state and any state in between of the material.

However, also for a proper implant, such as a breast implant, it is possible to supply a kit comprising an appropriately shaped pouch and a reconstitutible hydrogel or a hydrogel in a syringe, ready for use.

FIG. 1 illustrates schematically (not to scale) and in cross-section one embodiment of the invention in the form of a mammary implant 10, i.e. a replacement for a natural breast, e.g. for reconstructing the natural appearance after surgery, or for cosmetic purposes.

It comprises a container or pouch 12 made of a textile material. The pouch 12 contains a partially cross-linked, particulate hyaluronic acid 14.

The container can be made from one or multiple parts joined and finally sealed by welding (laser, ultrasonic) sintering, knitting, sewing or combinations thereof. Schematically indicated at 16 there are pores in the pouch (only a fraction of pores are shown). These pores can be the mesh of a woven or knitted fabric.

Filling the container can be made by syringe through the filter mesh or through any appropriate valve. Filling can be done prior to implanting or after the pouch has been put in place.

FIG. 2 illustrates a situation as discussed previously where a hydrogel particle 20, due to its viscoelastic properties can extend slightly 22 through pores 24, or a mesh between filaments 26 in case of a woven barrier)

In FIG. 3 another situation is illustrated. Here individual chains or at least moieties 30 of the bio-compatible material 20 on a molecular scale extend through the mesh or pore 24 to exhibit a bio-compatible entity on or at the surface of the implant.

FIG. 4 shows a situation where smaller fragments 40 of the bio-compatible material 20 and molecular level moities 42 have migrated through the pores or mesh 24, and resides, at least temporarily on or at the surface of the implant.

The invention will now be described by way of the following non-limiting examples.

EXAMPLES

In all Examples below a hydrogel of hyaluronic acid is obtained from Q-Med, Uppsala, Sweden.

All textiles used in the examples are commercially available.

Example 1

Test Implant

A pouch was made of Sefar Nitex™ textile (from Sefar AG, Switzerland), which is made from polyamide yarn having a yarn diameter of 86 μm (monofilament), and has a mesh size of 150 μm. The pouch was made by cutting a piece of textile by laser and forming the material into a pouch and finally sealing it by laser welding. The pouch was filled with the hydrogel particles by injecting the viscoelastic particles by a syringe.

Example 2

Pouches made as in Example 1 were filled with Restylane SubQ (Manufactured by Q-Med) using a 21 gauge syringe. No leakage at the injection site was observed. The surface of the pouches had a lubricious feeling indicating presence of the polysaccharide on the surface of the pouches.

Example 3

Pouches filled as in Example 2 were placed in a plastic jar containing water. After at least five months storage, the pouches were still filled with gel and the surface still had a lubricious feeling, indicating presence of the polysaccharide on the surface of the pouches.

Example 4

Pouches filled as in Example 2 were dried at room temperature. Pouches containing dried material were then placed in a tube containing access of water. The dry material swelled within an hour and the pouches regained the shape they had prior drying, filled with gel.

What is claimed is:

1. An implant comprising a macromolecular bio-compatible material, enclosed in a pouch made of a barrier material which is porous to allow moieties of the macromolecular bio-compatible material, when implanted, to be exposed through the barrier, wherein the macromolecular bio-compatible material is a particulate hydrogel, whereby the surface of the barrier is experienced by the body as an essentially non-foreign object, wherein the hydrogel particles have predefined irregular shapes with elongated portions and at least some of the elongated portions extend into and out from the pores in the pouch thereby forming a protective layer on an outside surface of the pouch that prevents or inhibits on-growth of cells, when the implant is implanted in the body.

2. The implant according to claim 1 which is a breast implant.

3. The implant according to claim 1 which is a buttocks implant.

4. The implant of claim 1, wherein the hydrogel is bioresorbable.

5. A kit, comprising a barrier in the form of a pouch and a macromolecular and bio-compatible material within the pouch, wherein the barrier material is porous to allow moieties of the macromolecular and bio-compatible material, when implanted, to be exposed through the barrier, wherein the macromolecular and bio-compatible material comprises hydrogel particles having predefined irregular shapes with elongated portions and at least some of the elongated portions extend into and out from the pores in the pouch thereby forming a protective layer on an outside surface of the pouch that prevents or inhibits on-growth of cells, when the pouch enclosing the macromolecular and bio-compatible material is implanted in the body.

6. The kit of claim 5, wherein the macromolecular bio-compatible material is a bioresorbable hydrogel.

7. An implantable combination comprising
a porous barrier comprising a sheet material selected from the group consisting of a woven fabric, a knitted fabric, a non-woven fabric, a perforated film and a discontinuous film, having openings extending through the sheet, the openings having an effective diameter in the range 0.02 mm to 5 mm, wherein the porous barrier is in the form of a pouch; and
a macromolecular bio-compatible material, wherein the macromolecular bio-compatible material is a hydrogel, said hydrogel being particulate, the particle size being between 0.1 mm to 10 mm, wherein the porous barrier allows moieties of the macromolecular bio-compatible material within the pouch, when implanted, to be exposed on and/or through the porous barrier, whereby the surface of the porous barrier is experienced by the body as an essentially non-foreign object, wherein the hydrogel particles have predefined irregular shapes with elongated portions and at least some of the elongated portions extend into and out from the pores in the pouch thereby forming a protective layer on an outside surface of the pouch that prevents or inhibits on-growth of cells, when the implantable combination is implanted in the body.

8. The implantable combination as claimed in claim 7, wherein the macromolecular bio-compatible material is a hydrogel of a polysaccharide.

9. The implantable combination as claimed in claim 8, wherein the polysaccharide is hyaluronic acid.

10. The implantable combination as claimed in claim 8, wherein the hydrogel is in a swollen state or in a dry state.

11. The implantable combination as claimed in claim 7, wherein the porous barrier is shaped to fit a desired location in a body in which it is to be implanted.

12. The implantable combination as claimed in claim 7, said pouch being shaped so as to be usable as a breast implant.

13. The implantable combination as claimed in claim 7, said pouch being shaped so as to be usable as a buttocks implant.

14. The implantable combination of claim 7, wherein the protective layer is sustained or continuously renewed over time, while the implantable combination is implanted in the body.

15. The implantable combination of claim 7, wherein the macromolecular bio-compatible material is bioresorbable.

16. The implantable combination of claim 7, wherein the implantable combination does not comprise a drug.

17. A depot device, for sustained or controlled release of a drug or other beneficial agent, comprising
a) a barrier in the form a pouch;
b) a macromolecular and bio-compatible material within the pouch;
c) a drug distributed in the macromolecular and bio-compatible material;
wherein the barrier material is porous to allow moieties of the macromolecular and bio-compatible material, when implanted, to be exposed through the barrier, whereby the surface of the barrier is experienced by the body as an essentially non-foreign object, and to allow the drug to be released through the barrier, wherein the macromolecular and bio-compatible material comprises hydrogel particles having predefined irregular shapes with elongated portions and at least some of the elongated portions extend into and out from the pores in the pouch thereby forming a protective layer on an outside surface of the pouch that prevents or inhibits on-growth of cells, when the depot device is implanted in the body.

18. A method of body contouring, comprising implanting an implantable combination as claimed in claim 7 in a desired location in a body, by minimal invasive surgery.

* * * * *